United States Patent [19]

Ueda et al.

[11] Patent Number: 4,575,548

[45] Date of Patent: Mar. 11, 1986

[54] OCCLUSION COMPOUND OF 2-NITROXYMETHYL-6-CHLOROPYRIDINE WITH β-CYCLODEXTRIN AND PROCESS FOR PREPARATION THEREOF

[75] Inventors: Yoshio Ueda, Mikagenakamachi; Fumio Shimojo, Kawanishi; Kiyoshige Yoshida, Mino, all of Japan

[73] Assignee: Fujisawa Pharmaceutical Co., Ltd., Osaka, Japan

[21] Appl. No.: 654,471

[22] Filed: Sep. 26, 1984

[30] Foreign Application Priority Data

Oct. 11, 1983 [JP] Japan .................. 58-190345

[51] Int. Cl.⁴ .................. C08B 37/16; A61K 31/73
[52] U.S. Cl. .................. 536/46; 536/103
[58] Field of Search .................. 536/46, 103

[56] References Cited

U.S. PATENT DOCUMENTS

| | | | |
|---|---|---|---|
| 2,959,580 | 11/1960 | Schlenk et al. | 536/103 |
| 3,420,788 | 1/1969 | Solms | 536/103 |
| 4,365,061 | 12/1982 | Szejtli et al. | 536/103 |
| 4,425,336 | 1/1984 | Tuttle | 536/46 |
| 4,482,709 | 11/1984 | Iwao et al. | 536/46 |

FOREIGN PATENT DOCUMENTS 58-67670  4/1983  Japan .................. 536/46

OTHER PUBLICATIONS

Dissertation Abstracts International, vol. 41, No. 6, Dec. 1980, p. 2127–B.

Primary Examiner—Ronald W. Griffin
Attorney, Agent, or Firm—Oblon, Fisher, Spivak, McClelland & Maier

[57] ABSTRACT

An occlusion compound of 2-nitroxymethyl-6-chloropyridine with β-cyclodextrin is disclosed herein as well as a process for preparing the occlusion compound thereof. The occlusion compound of the present invention has a molar ratio of 2-nitroxymethyl-6-chloropyridine to β-cyclodextrin of between about 1:1 and about 3:1. The present occlusion compound is non-volatile, thereby overcoming the problems associated with the volatility of the 2-nitroxymethyl-6-chloropyridine for pharmacuetical preparations. The process of the present invention is carried out by reacting 2-nitroxymethyl-6-chloropyridine with β-cyclodextrin either by kneading both compounds together with a small amount of a solvent or by mixing both compounds in an appropriate solvent, such as water. The occlusion compound is then precipitated, separated and further purified by conventional methods.

6 Claims, 5 Drawing Figures

OCCLUSION COMPOUND OF 2-NITROXYMETHYL-6-CHLOROPYRIDINE WITH β-CYCLODEXTRIN AND PROCESS FOR PREPARATION THEREOF

BACKGROUND OF THE INVENTION

FIELD OF THE INVENTION

This invention relates to an occlusion compound of 2-nitroxymethyl-6-chloropyridine with β-cyclodextrin and to a process for preparing the occlusion compound thereof.

DESCRIPTION OF THE PRIOR ART

2-Nitroxymethyl-6-chloropyridine is a compound having the structural formula given below and is useful as a drug for the treatment of vascular disorders.

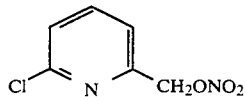

2-Nitroxymethyl-6-chloropyridine is an oily and volatile substance. It is in general difficult to make up such substance into a pharmaceutical preparation.

SUMMARY OF THE INVENTION

As a result of their intensive study conducted so as to overcome the above difficulty, the present inventors found that the difficulty can be overcome by converting 2-nitroxymethyl-6-chloropyridine to its occlusion compound with β-cyclodextrin in a molar ratio of about 1:1 or about 3:1.

The present invention has thus successfully solved not only the problem of making a powder preparation of 2-nitroxymethyl-6-chloropyridine but also the problem of preventing its volatility.

The process of the present invention is carried out by reacting 2-nitroxymethyl-6-chloropyridine with β-cyclodextrin.

DESCRIPTION OF THE INVENTION

The process of occlusion includes several modifications. For instance, there are a solvent process, a process comprising kneading the host and guest compounds together with a small amount of a solvent, etc. Among them preferred is the solvent process which only requires mixing both compounds in an appropriate solvent. The occlusion compound as obtained is isolated and purified by conventional methods. For instance, when the occlusion reaction is carried out in aqueous solution, the occlusion compound, which is sparingly soluble in water, precipitates from the reaction mixture. The precipitate can be separated by conventional methods, such as centrifugation. The thus separated product may be purified by washing with water, whereby β-cyclodextrin or 2-nitroxymethyl-6-chloropyridine which is water soluble is removed.

Figure 5:
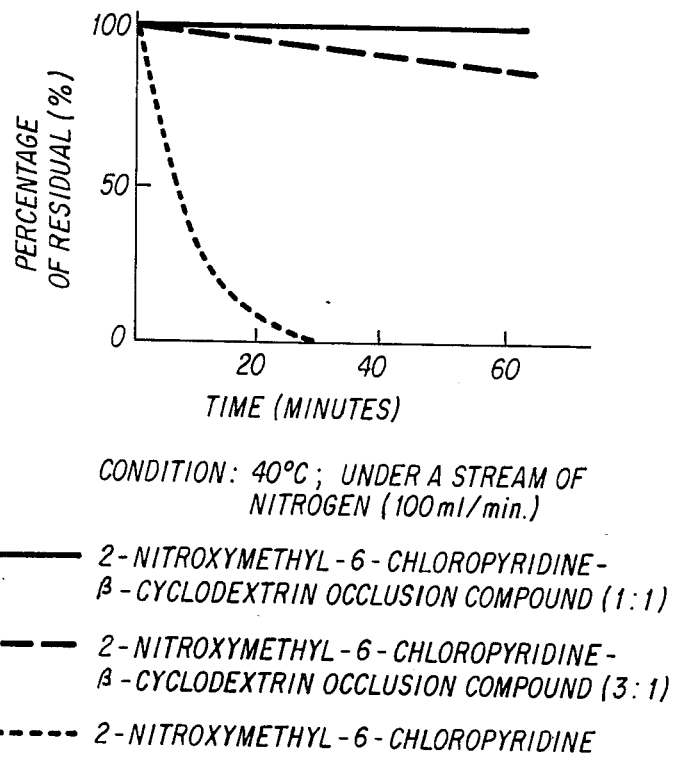
FIG. 5 illustrates the influence of the occlusion on the volatility of 2-nitroxymethyl-6-chloropyridine.

The occlusion compound obtained in the above process is characterized by preventing volatilization of 2-nitroxymethyl-6-chloropyridine. This is evidenced in FIG. 5 showing the percentage of residual 2-nitroxymethyl-6-chloropyridine as a function of time. 100% of the 2-nitroxymethyl-6-chloropyridine-β-cyclodextrin occlusion compound (molar ratio of 1:1) or about 87% of the 2-nitroxymethyl-6-chloropyridine-β-cyclodextrin occlusion compound (molar ratio of 3:1) remain after standing for 60 minutes. On the contrary, with 2-nitroxymethyl-6-chloropyridine per se, the residual percentage after 60 minutes is 0%. As clear from this, the volatility of 2-nitroxymethyl-6-chloropyridine is greatly prevented.

The following examples are further illustrative of the process of this invention.

EXAMPLES

Example 1

In each of five centrifuge tubes, 600 mg of β-cyclodextrin was dissolved in 20 ml of distilled water. Following addition of 50, 100, 200, 300, and 400 mg of 2-nitroxymethyl-6-chloropyridine to the five centrifuge tubes, respectively, the mixtures were shaken, centrifuged and allowed to stand overnight at room temperature so as to complete crystallization.

The crystals were collected by filtration, washed with water and air-dried and an occlusion compound of 2-nitroxymethyl-6-chloropyridine with β-cyclodextrin was obtained.

The conditions for preparing the occlusion compound of 2-nitroxymethyl-6-chloropyridine with β-cyclodextrin and the molar ratios found in the products are shown in Table 1 below.

The thus obtained occlusion compound has the following physical properties.

(i) Its X ray powder diffraction pattern shows peaks at 11.5°, about 17.2° and 18.4°. Such peaks are characteristic of an occlusion compound of 2-nitroxymethyl-6-chloropyridine with β-cyclodextrin.

(ii) Its infrared absorption spectrum (Nujol) shows absorptions at 3300, 1645, 1586, 1568, 1459, 1376, 1330, 1281, 1158, 1080, 1022, 1000, 940 and 842 cm$^{-1}$;

(iii) The occlusion compound is sparingly soluble in water.

TABLE 1

| Conditions of preparing an occlusion compound and molar ratios | | | |
| --- | --- | --- | --- |
| Composition of mixture solution (in 20 ml of distilled water) | | Content of 2-nitroxymethyl-6-chloropyridine in occlusion compound as obtained (%) | β-Cyclodextrin/ 2-nitroxymethyl-6-chloropyridine molar ratio in occlusion compound as obtained |
| Quantity of β-cyclodextrin added (mg) | Quantity of 2-nitroxymethyl-6-chloropyridine (mg) | | |
| 600 | 50 | 15.3 | 1/1.1 |

TABLE 1-continued

Conditions of preparing an occlusion compound and molar ratios

| Composition of mixture solution (in 20 ml of distilled water) | | Content of 2-nitroxy-methyl-6-chloropyridine in occlusion compound as obtained (%) | β-Cyclodextrin/ 2-nitroxymethyl-6-chloropyridine molar ratio in occlusion compound as obtained |
|---|---|---|---|
| Quantity of β-cyclo-dextrin added (mg) | Quantity of 2-nitroxymethyl-6-chloropyridine (mg) | | |
| | 100 | 14.5 | 1/1.0 |
| | 200 | 16.8 | 1/1.2 |
| | 300 | 34.2 | 1/3.1 |
| | 400 | 34.2 | 1/3.1 |

Figure 1:
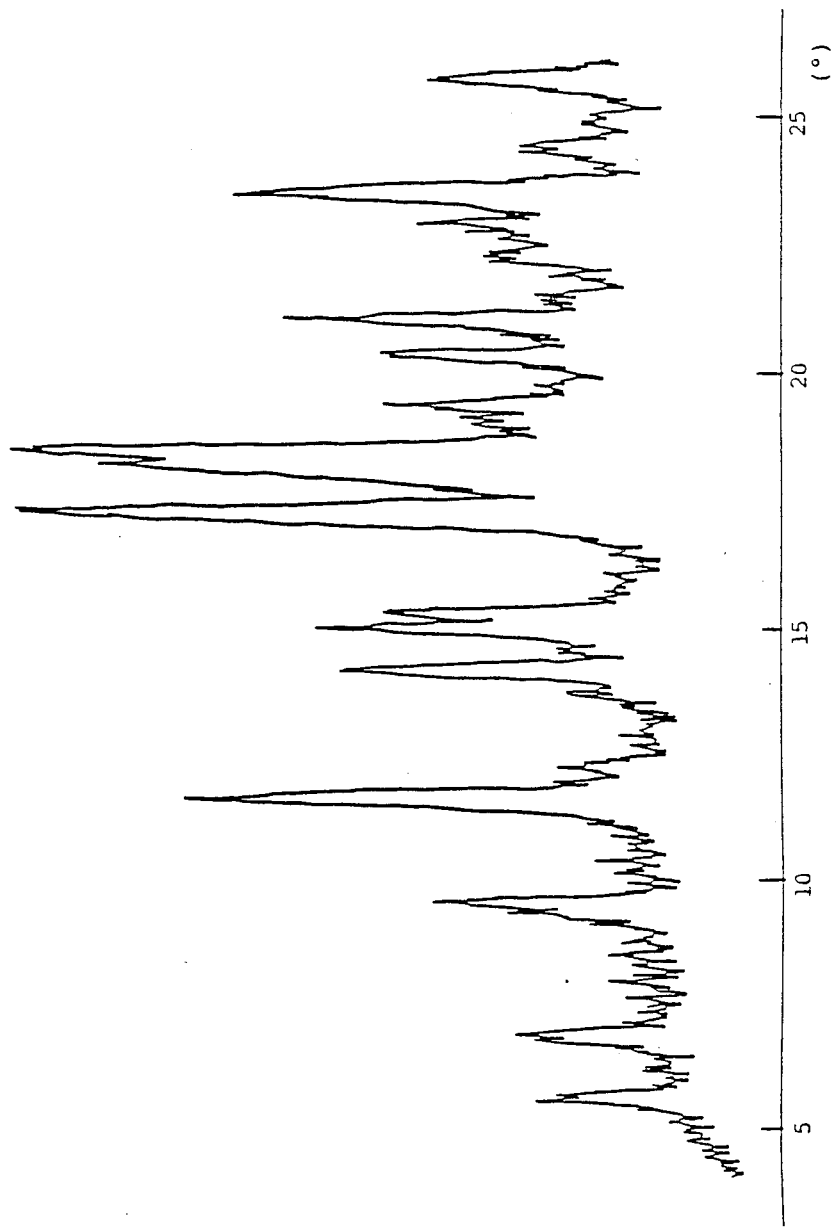
FIG. 1 and FIG. 2 are X ray powder diffraction patterns of the occlusion compounds obtained in Example 1 in accordance with this invention, namely the occlusion compounds of 2-nitroxymethyl-6-chloropyridine with β-cyclodextrin in the molar ratios of 1:1 and 3:1, respectively.
Figure 2:
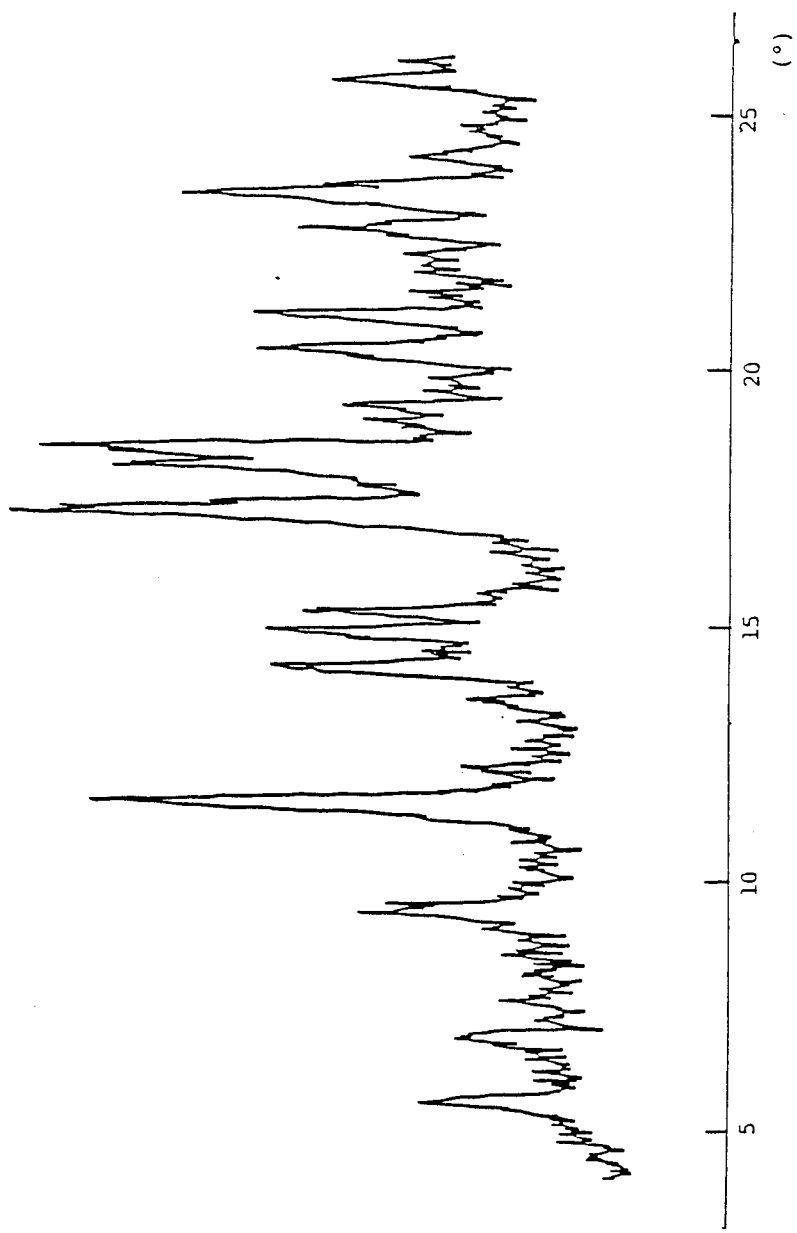
Figure 3:
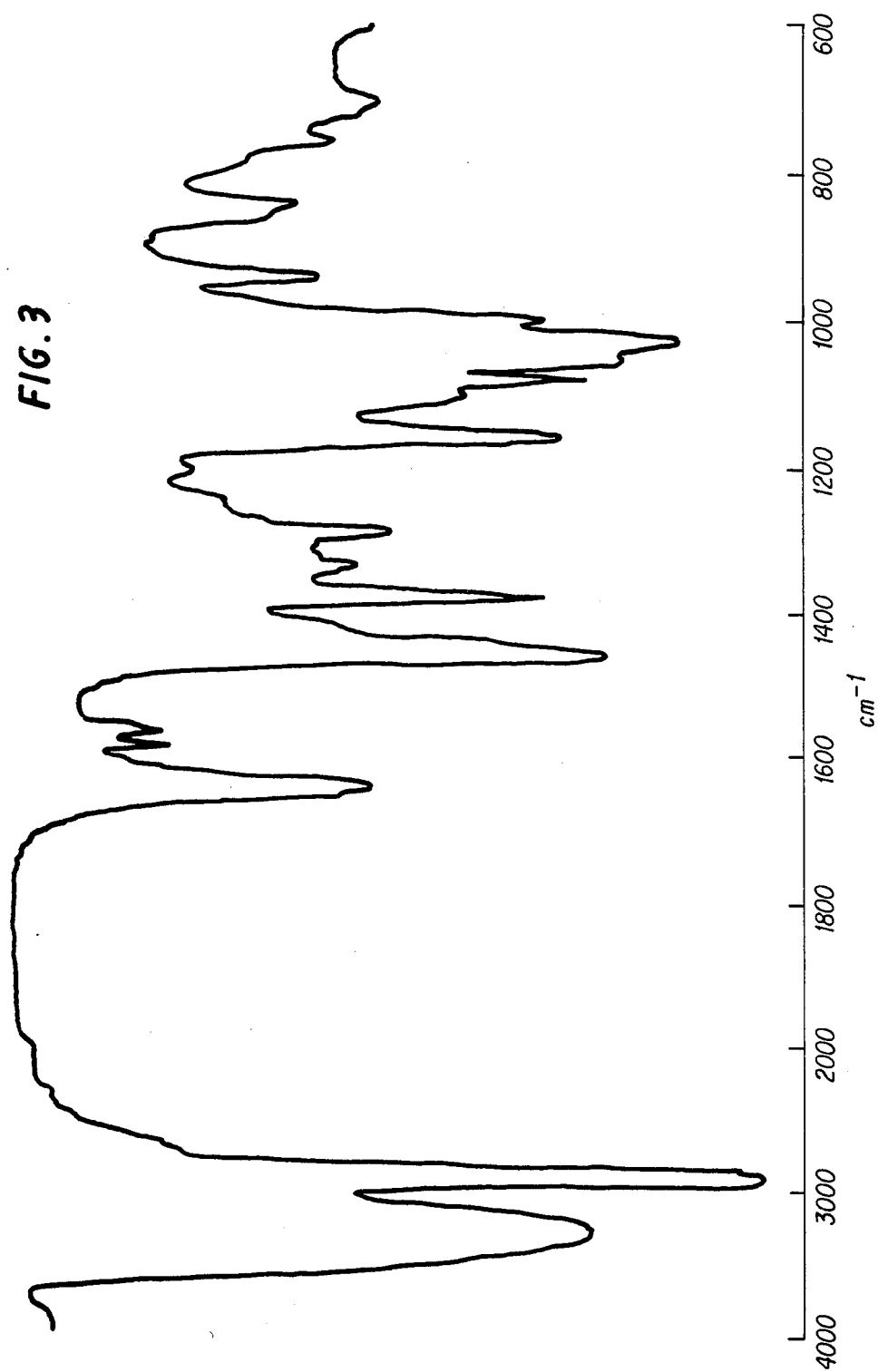
FIG. 3 and FIG. 4 are infrared absorption spectra of the occlusion compounds of this invention in the molar ratios of 1:1 and 3:1, respectively.
Figure 4:
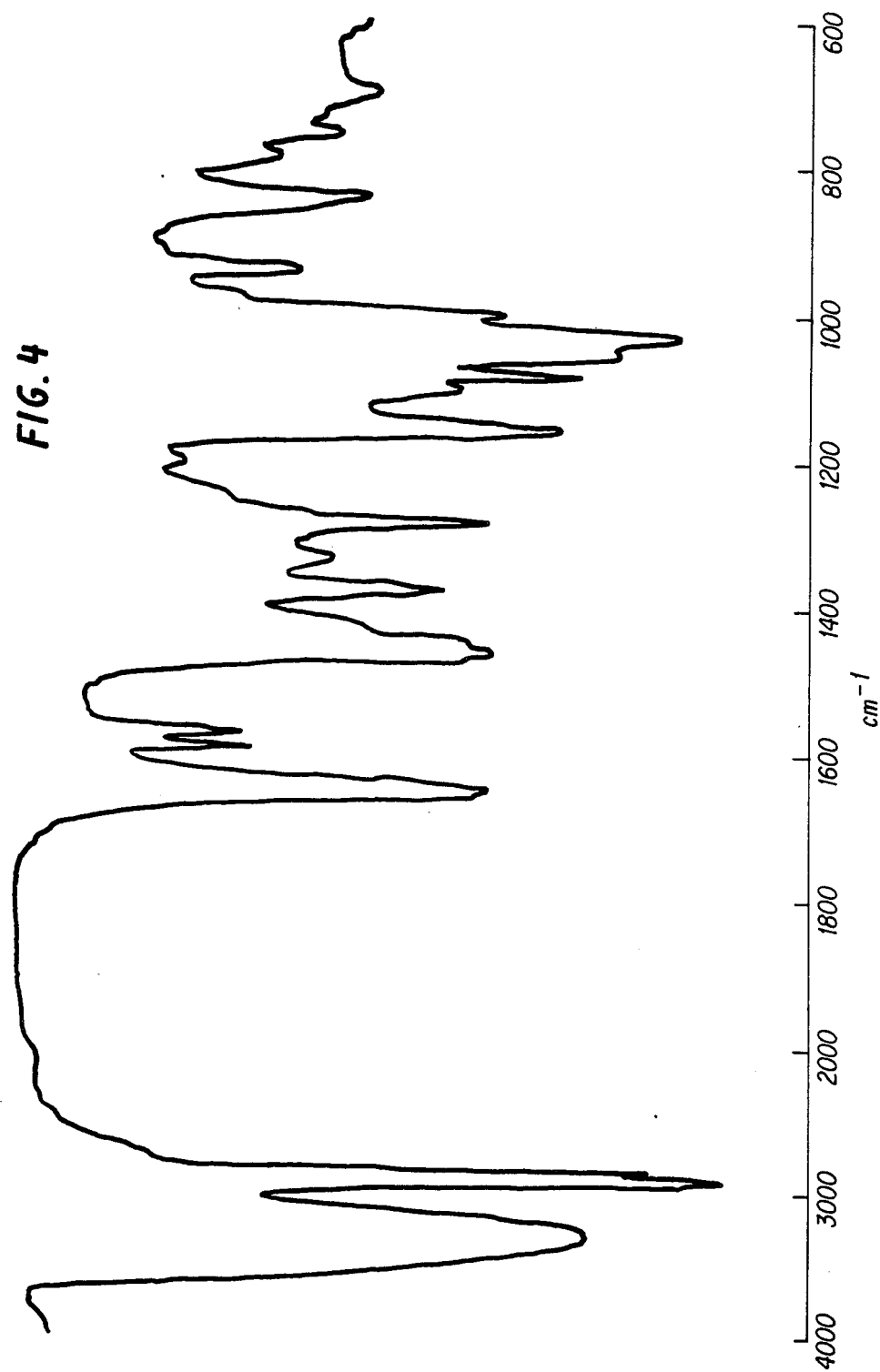

The X-ray powder diffraction patterns of these products are shown in FIG. 1 and FIG. 2 and the infrared absorption spectra thereof are shown in FIG. 3 and FIG. 4.

What we claim is:

1. An occlusion compound of 2-nitroxymethyl-6-chloropyridine with β-cyclodextrin.

2. The occlusion compound of claim 1 which has the following physical properties:
   (i) its X ray powder diffraction pattern is characterized by peaks at about 11.5°, 17.2° and 18.4°;
   (ii) its infrared absorption spectrum (Nujol), is characterized by absorption peaks at about 3300, 1645, 1586, 1568, 1459, 1376, 1330, 1281, 1158, 1080, 1022, 1000, 940 and 842 cm$^{-1}$;
   (iii) the occlusion compound is sparingly soluble in water water.

3. The occlusion compound of claim 1 wherein the molar ratio of 2-nitroxymethyl-6-chloropyridine to β-cyclodextrin is between about 1:1 and 3:1.

4. A process for preparing an occlusion compound of 2-nitroxymethyl-6-chloropyridine with β-cyclodextrin comprising
   (a) admixing 2-nitroxymethyl-6-chloropyridine with an aqueous solution of β-cyclodextrin;
   (b) allowing for the occlusion compound to precipitate; and
   (c) separating the precipitated occlusion compound from the aqueous solution.

5. The process of claim 4, wherein step (c) is carried out by centrifugation.

6. The process of claim 4 further comprising:
   (d) washing the separated occlusion compound with water in order to remove impurities.

* * * * *